United States Patent [19]

Blumenthal et al.

[11] Patent Number: 5,362,627
[45] Date of Patent: Nov. 8, 1994

[54] STABILIZATION AND REDUCTION OF BACKGROUND FLUORESCENCE OF HYDROXY COUMARIN ESTER ENZYME SUBSTRATES

[75] Inventors: Richard A. Blumenthal, Charlestown, Mass.; Hon-Peng P. Lau, Hockessin; Esther K. Yang, Wilmington, both of Del.

[73] Assignee: E. I. Du Pont de Nemours and Company, Wilmington, Del.

[21] Appl. No.: 242,598

[22] Filed: Sep. 12, 1988

[51] Int. Cl.⁵ .................... G01N 33/53; C12Q 1/44
[52] U.S. Cl. ........................ 435/7.9; 435/18; 435/19; 435/183; 435/195; 435/196; 436/8
[58] Field of Search .............. 435/7, 14, 18, 19, 21, 435/34, 38, 808, 7.9, 183, 195, 196; 436/547, 8; 542/296; 549/283, 290

[56] References Cited

U.S. PATENT DOCUMENTS

| | | | |
|---|---|---|---|
| 3,466,306 | 9/1969 | Babson | 435/21 |
| 3,553,235 | 1/1971 | Kircher et al. | 549/289 |
| 4,378,458 | 3/1983 | Gohlke et al. | 536/27 |
| 4,591,554 | 5/1986 | Koumura et al. | 435/18 |
| 4,659,657 | 4/1987 | Harnisch et al. | 435/18 |
| 4,661,444 | 4/1987 | Li | 435/25 |

FOREIGN PATENT DOCUMENTS

| | | |
|---|---|---|
| 0009222 | 4/1980 | European Pat. Off. |
| 1668440 | 12/1966 | Germany |
| 2133007 | 7/1984 | United Kingdom |

OTHER PUBLICATIONS

Harnisch et al. –Chem. Abst. vol. 101 (1984) p. 230, 362C.
Kircher et al. –Chem. ABst. vol. 74 (1971) p. 141, 530n.
Fujii et al. –Chem. Abst. vol. 77 (1972) p. 164, 482z.
O'Neal et al.–Chem. Abst. vol. 98 (1983) p. 40510w.
Guilbault et al., *Anal. Chem.*, vol. 41, 2006–2009, 1969.
Mattoo, *Trans. Faraday Soc.*, 1957, 53, 760–766.
Fernley et al., *Biochem. J.*, vol. 97, 95–103 (1965).
Fink et al., *Analytical Chemistry*, 42, 990–993 (1970).
Mattoo, *Trans. Faraday Soc.*, 1958, 54, 19–24.
Birkmeyer et al., *Clin. Chem.*, 33(9): 1543–1547 (Sep. 1987).
Aldersley et al., *Tetrahedron* 43(22):5417–5429 (1987).

*Primary Examiner*—Toni R. Scheiner

[57] ABSTRACT

Hydroxy coumarin ester enzyme substrates can be stored in a strong base at pH above 11 to stabilize the substrate against premature hydrolysis of the ester bond and to reduce the revel of contaminating hydroxy coumarin. When diluted in buffer at pH below 11 shortly before use in an enzyme assay, the substrate solution provides low background fluorescence.

10 Claims, 4 Drawing Sheets

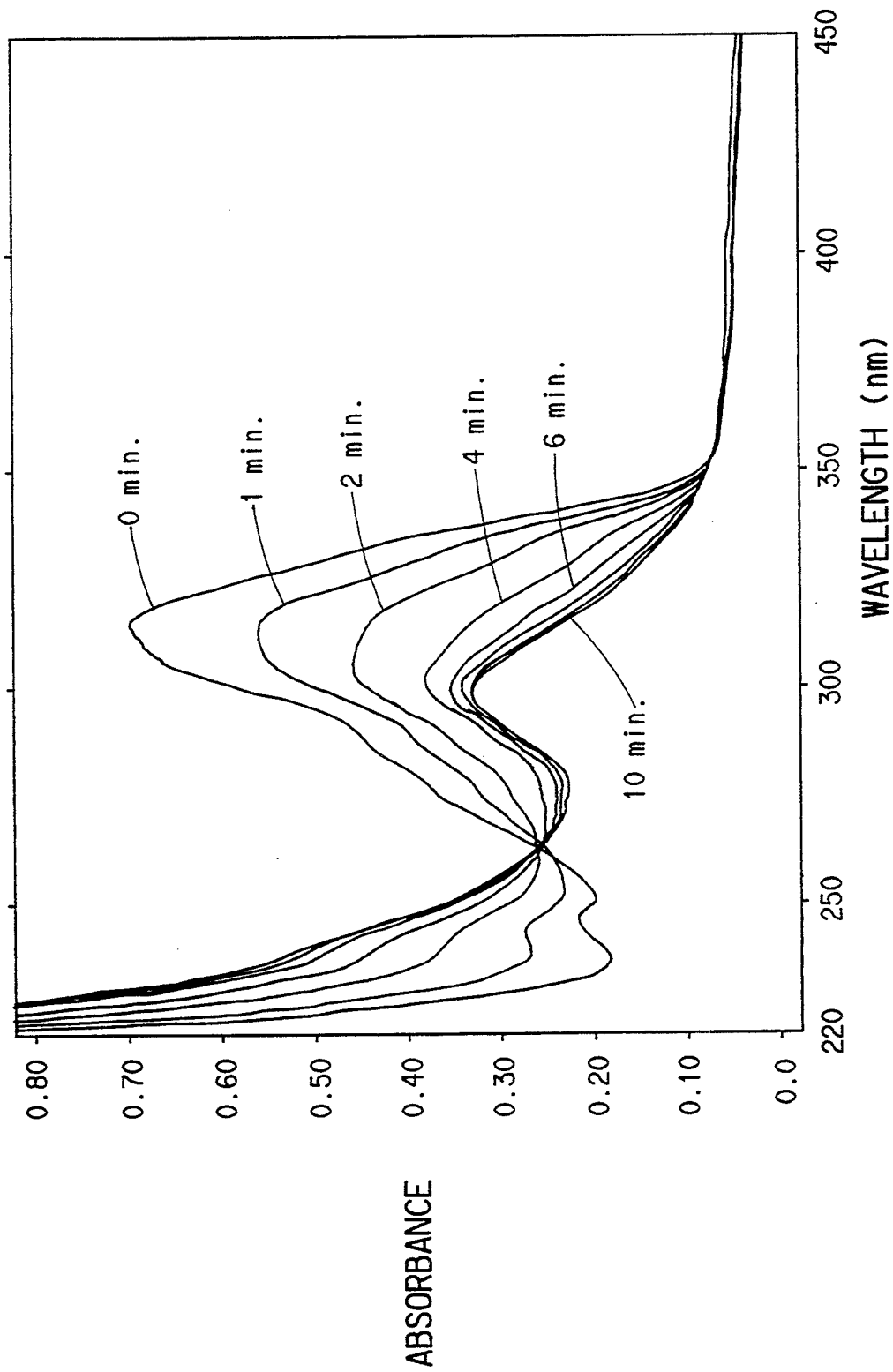

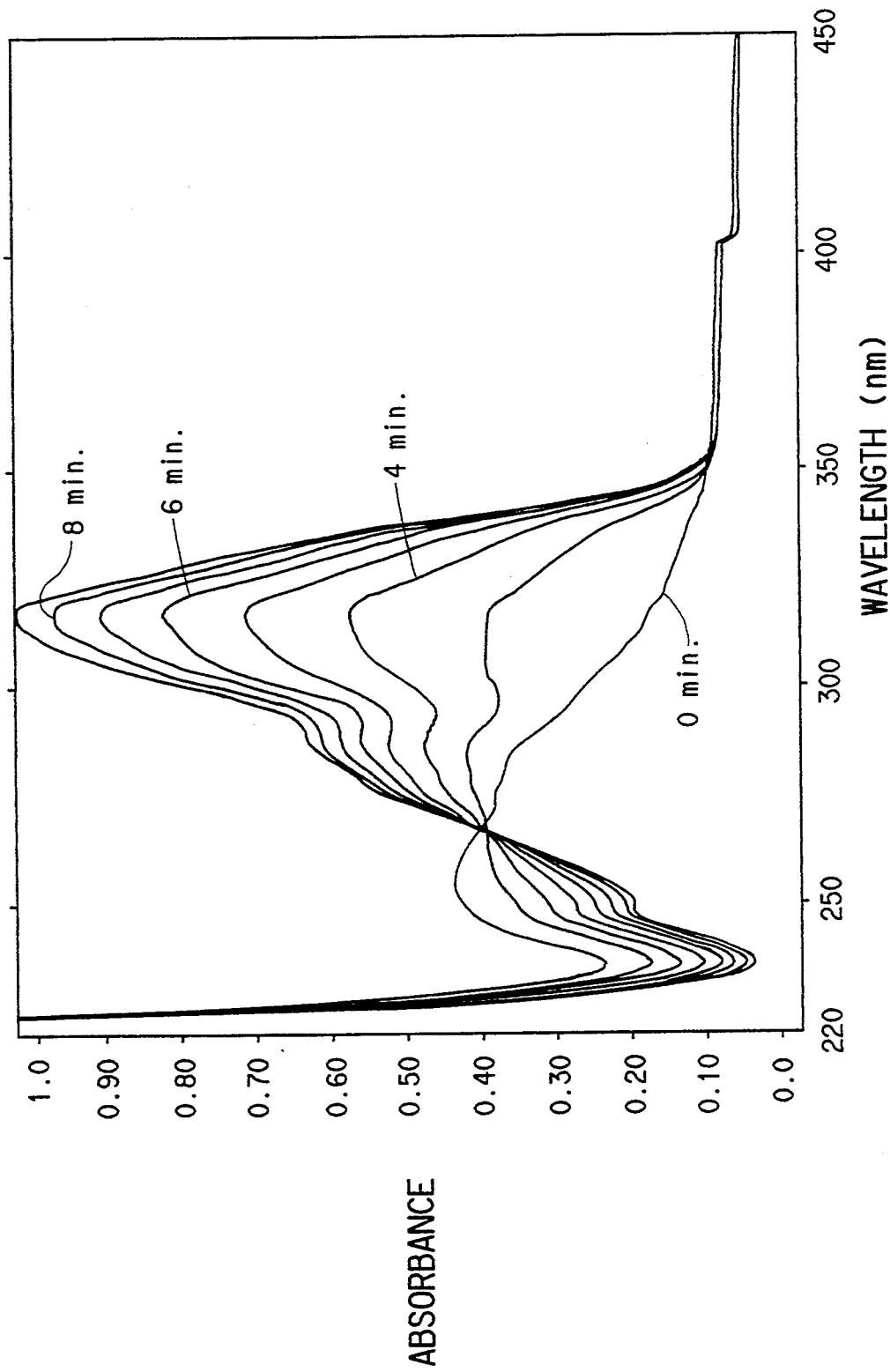

STABILIZATION AND REDUCTION OF BACKGROUND FLUORESCENCE OF HYDROXY COUMARIN ESTER ENZYME SUBSTRATES

TECHNICAL FIELD

This invention relates to the stabilization and reduction of the background fluorescence of enzyme substrates containing hydroxy coumarin esters in aqueous solution. More particularly, this invention relates to storing said substrates in a strong base to stabilize the substrate against hydrolysis of the ester bond and reduce the background fluorescence resulting from the hydroxy coumarin hydrolysis product in the substrate.

BACKGROUND ART

Enzymes are widely used as labels in immunoassays and DNA probe assays. In order to achieve good performance, the enzyme must be stable, highly reactive, available in high specific activity, easy to conjugate to other proteins or haptens and safe to use. In addition, a suitable substrate for the enzyme must be readily available. The requirements of a suitable substrate include high sensitivity of the reaction product (i.e., high extinction coefficient or high fluorescence), low background signal (i.e., low starting absorbance or low starting fluorescence) and good stability (i.e., substrate does not decompose to give chromophore or fluorophore absorbing at the measurement wave length unless enzyme is present). These requirements are particularly important for automated assays which require minimum calibration frequency.

The stability of an enzyme substrate can be thought of in terms of the amount of time that the substrate can be used as a substrate in a particular enzyme assay. Factors that influence the useful lifetime of a substrate include the chemical stability of the substrate in the milieu it is stored in, the amount of background signal (i.e., fluorescence, absorbance, etc.) present in the substrate preparation and the amount of signal being detected in the enzyme assay.

Substrate background is the signal generated from the substrate degradation products. These degradation products can result from impurities generated during the synthesis and purification of the substrate, from breakdown of the substrate (instability) during storage or from product formed during an assay in the absence of the enzyme. Although some background signal from the substrate can be tolerated, high background signals relative to the specific signal being detected in the assay will result in poor assay performance.

Poor substrate stability will result in using suboptimal substrate concentrations since the initial substrate concentration (and background signal) must be low enough to allow for the continuously increasing background signal caused by the instability. The high, changing background will require more frequent instrument blanking and make accurate measure of enzyme activity more difficult.

Among many commonly used fluorescent enzyme substrates, 4-methyl umbelliferyl esters offer high sensitivity and are readily available for many enzymes. 4-Methyl umbelliferyl esters are fluorescent but at a shorter wavelength than the hydrolyzed product, i.e., 4-methyl umbelliferone. Thus, the spectral interference can be minimized by selecting the measurement wavelength optimal for the 4-methyl umbelliferone product. However, the instability and high background fluorescence of methyl umbelliferyl esters have limited their wide application in commercial products. Methyl umbelliferyl esters are part of a larger class of compounds known as hydroxy coumarin esters.

B. N. Mattoo (Trans. Faraday Soc., 1957, 53, 760–766) describes the structural changes of coumarin at high pH, but the reverse reaction is not discussed. Mattoo does not discuss the stability of coumarin or of hydroxy coumarin esters.

In Trans. Faraday Soc., 1958, 54, 19–24, Mattoo discusses the dissociation constants of hydroxy coumarins. Mattoo does not discuss the stability of hydroxy coumarins or the reduction of their fluorescence in high concentrations of base.

Fernley et al., in Biochem. J., Vol. 97, 95–103 (1965), discuss the use of 4-methyl umbelliferyl phosphate (MUP) as a substrate for the measurement of calf intestinal phosphatase activities. They detail the kinetic behavior of the enzyme as a function of pH, ionic strength and temperature. The MUP was dissolved in 0.5M $K_2HOP_4$-KOH buffer, pH 10.4, and used in the phosphatase assay at various pH values in the range of 7.55 to 10.4.

In Analytical Chemistry, 42, 990–993 (1970), Fink et al. discuss the effect of pH on the fluorescence properties of umbelliferone. Fink et al. do not use pH values higher than 12.7 (0.05N NaOH) and they do not discuss the stability of umbelliferyl esters.

In U.S. Pat. No. 3,466,306, issued Sep. 9, 1969 Babson et al. describe the stabilization of certain phosphate ester substrates in an alkaline buffer of pH 9.7 to 10.5. Babson et al. do not mention 4-methyl umbelliferyl phosphate as a compound to be stabilized by their method. Also, while the method of Babson et al. slows down the hydrolysis of phosphate esters, it does not make long-term storage of 4-methyl umbelliferyl phosphate feasible. Because of the high fluorescence sensitivity of 4-methyl umbelliferone, a trace hydrolysis of 4-methyl umbelliferyl phosphate will result in an unacceptably high background signal.

There still exists a need for compositions and methods which will provide a very stable storage milieu for hydroxy coumarin esters in general and methyl umbelliferyl esters specifically while at the same time providing for a reduction in the background fluorescence due to contaminating hydrolysis products. This invention provides such compositions and methods.

SUMMARY OF THE INVENTION

In one embodiment, this invention is a method of stabilizing a hydroxy coumarin ester against hydrolysis to a hydroxy coumarin and further degradation to nonfluorogenic compounds which comprises dissolving the ester in water containing a strong base in sufficient concentration to stabilize the ester against hydrolysis. The amount of base should be sufficient to provide a solution pH of 11 or greater, preferably 12.5 or greater, depending on the particular ester. Since hydroxy coumarin esters are usually initially contaminated with hydroxy coumarins, the solution is preferably aged long enough before use to substantially eliminate hydroxy coumarin from the solution. The solution can be dried to powder form and the powder can be tabletted if desired. For use in an enzyme assay, the solution, or tablet is diluted or dissolved in buffer solution at pH below 11, preferably $\leq$ about 9, to provide a solution substantially free of hydroxy coumarin. Thus, the hydroxy coumarin ester solutions of this invention provide exceptionally low background singal in enzyme assays.

This invention in another embodiment is an improvement in a conventional enzyme assay method wherein (a) an esterase-labelled reagent is mixed with a sample and reacts directly or indirectly with any analyte present in the sample, or competes with any analyte present for reaction with another reagent, (b) a hydroxy coumarin ester substrate for the esterase, in buffer solution at pH<11, is added whereby any esterase present hydrolyzes the ester to a hydroxy coumarin, arid (c) the enzyme reaction is quenched and fluorescence of the solution is measured at a wavelength which is optimal for the hydroxy coumarin. The improvement comprises reducing background fluorescence by (A) providing a solution, powder or tablet which has been prepared by mixing a hydroxy coumarin ester with a strong base as described above, (B) diluting the solution or dissolving the tablet in buffer at pH<11, and (C) using the resulting solution in step (b) above before formation of any substantial amount of hydroxy coumarin.

We do not want to be bound or limited by theory, but we offer the following probable explanation for the results obtained in this invention. Spectral data indicate that the hydroxy coumarin esters and hydroxy coumarins undergo a structural change in the presence of strong base. The structural change is believed to involve an opening of the coumarin ring to produce non-fluorogenic molecules. The open ring esters are stable in the presence of strong base. The change occurs faster in the esters than in the hydroxy coumarins, thus the need for aging to substantially eliminate contaminating hydroxy coumarins. In the case of the esters the change is readily reversed, and the original closed ring ester is rapidly regenerated by diluting the base solution into an enzyme buffer at pH below 11. At lower pH the regeneration is even faster. The hydroxy coumarins are also regenerated by diluting the base solution, but at a much slower rate compared to the typical enzyme assay time of several minutes. Furthermore, at least some of the hydroxy coumarin may be degraded to molecules which cannot be reconverted to hydroxy coumarin, Thus, it is possible to store the hydroxy coumarin ester in a strong base to improve stability and reduce the background due to contaminating hydroxy coumarin.

DESCRIPTION OF THE DRAWINGS

FIGS. 1, 2, 3 and 4 show the spectral data referred to above. Each figure shows a family of curves obtained by measuring absorbance at various wavelengths in the range of 220–450 nm and at various times. FIGS. 1 and 3 indicate that structural changes occur in MUP and 4-methyl umbelliferyl $\beta$-D-galactopyranoside (MUG) when placed in a solution of sodium hydroxide. FIGS. 2 and 4 indicate that the structural changes are reversed when the solution is diluted in TRIS buffer.

DESCRIPTION OF THE INVENTION

Figure 1:
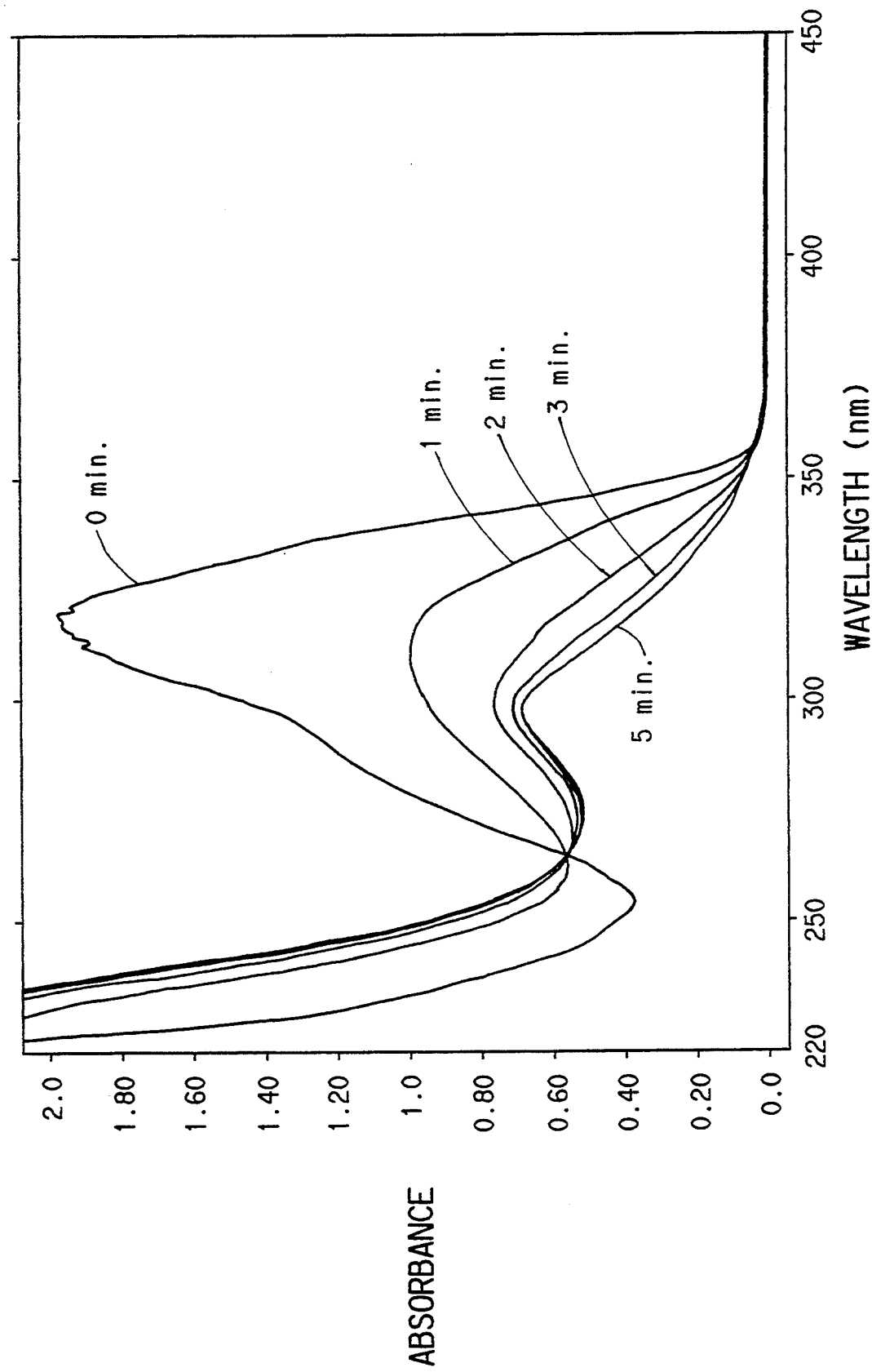
Figure 2:
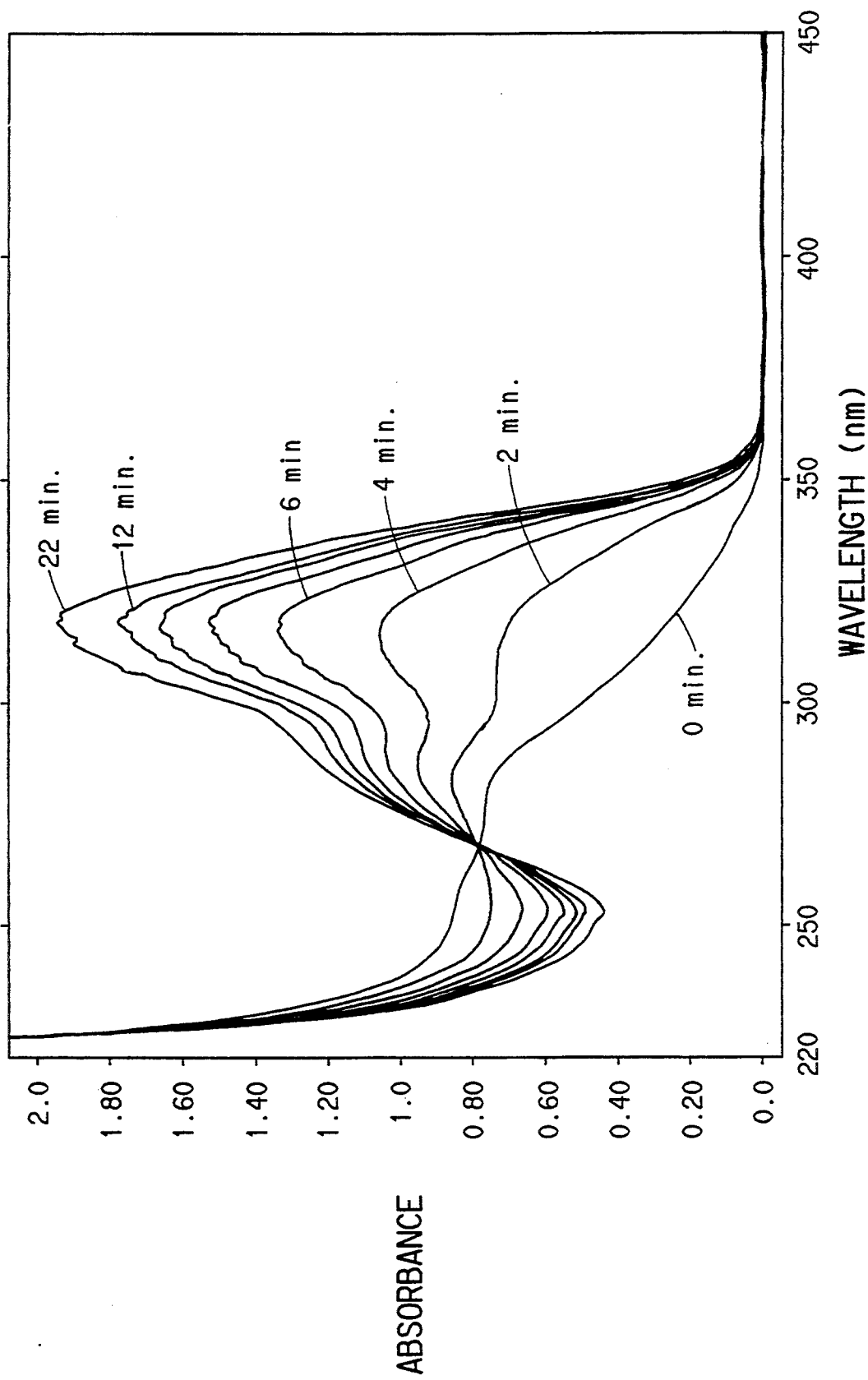

The present invention is based on the surprising discovery that the enzyme substrate 4-methyl umbelliferyl phosphate becomes very stable to hydrolysis when it is stored in a strong base. In addition, the background fluorescence caused by contaminating 4-methyl umbelliferone is virtually eliminated. The 4-methyl umbelliferyl phosphate stored by the process of this invention is readily available as an enzyme substrate when it is diluted into a typical enzyme assay milieu with enough buffering capacity to bring the pH of final assay milieu into a suitable enzyme assay pH range. Thus, it is possible to store the enzyme substrate 4-methyl umbelliferyl phosphate in a strong base to improve stability and reduce the background fluorescene due to contaminating 4-methyl umbelliferone.

Many hydroxy coumarin esters and their salts can be stabilized and their background reduced using the process of the instant invention. These include esters of 7-hydroxy-4-methyl coumarin (i.e., 4-methyl umbelliferyl), 7-hydroxy coumarin, 6-hydroxy coumarin, 5-hydroxy-4-ethyl coumarin, 5-hydroxy coumarin and derivatives prepared from these compounds. Other hydroxy coumarin esters which can be used with the instant invention will be apparent to the skilled artisan given the teachings herein.

The preferred hydroxy coumarin esters are esters of 7-hydroxy-4-methylcourmarin (4-methyl umbelliferyl esters). These include but are not limited to the phosphate, acetate, sulfate, oleate, p-guanidinobenzoate, $\beta$-D-galactopyranoside, and $\beta$-D-N,N',N'-triacetyl-chitotriose esters and salts thereof.

Any strong base can be used to stabilize hydroxy coumarin esters according to this invention. Common alkali metal hydroxides such as sodium hydroxide, potassium hydroxide, and lithium hydroxide, as well as alkali metal carbonates and silicates, can all be used. Guanidine, ammonium hydroxide and alkylamines such as methylamine are examples of various non-metallic bases which can be used. For purpose of this invention, a strong base is defined as any base having a pK' of 10 or greater.

The concentration of strong base needed to practice the invention depends on the concentration of hydroxy coumarin to be stabilized and the storage temperature. In general, the base concentration should be sufficient to bring the final solution of the hydroxy coumarin ester and base up to a pH$\geq$11. Some hydroxy coumarin esters require higher pH for stabilization, especially for storage at elevated temperature. For example, in the case of MUP the pH for storage at 4° C. is preferably $\geq$ about 12.5, whereas the pH for storage at 37° C. is preferably $\geq$ about 13. For all hydroxy coumarins, it is expected that pH$\geq$12, preferably pH$\geq$13, will provide best results. More preferably, alkali metal hydroxide concentration of 0.1N to 1.0N should be used. Higher concentrations of metal hydroxide can be used for some hydroxy coumarins. Using strong base in too high concentration may destroy some hydroxy coumarin esters, so pH below about 13.5 is generally preferred. The preferred base to stabilize hydroxy coumarin esters according to the instant invention is sodium hydroxide at a concentration of 0.5N.

Although the background fluorescence of a hydroxy coumarin ester solution is significantly reduced after it is in contact with a strong base for only a short time, the time required to achieve minimum background depends on the type and concentration of the contaminating hydroxy coumarin, the concentration of the base used and the storage temperature. By background fluorescence we mean the fluorescence of the solution after it has been diluted in buffer at pH below 11 in order to regenerate hydroxy coumarin ester. By minimum background we mean background fluorescence which is not further substantially reduced upon continued aging in strong base at pH above 11. In the case of MU, for example, minimum background is the fluorescence equivalent to about $5 \times 10^{-9}$ mole of MU when tested in the Sequoia-Turner Model 400 fluorometer. We believe that aging in strong base initially converts contaminating hydroxy coumarin as well as hydroxy coumarin ester to open ring non-fluorogenic molecules which revert to the original, closed ring coumarins upon dilution in buffer at pH below 11. We believe that continued aging in strong base converts the contaminating hydroxy coumarin irreversibly to non-fluorogenic structure, resulting in minimum background. Aging for up to five days at room temperature is adequate to achieve minimum background fluorescence for the MUP free acid obtained from JBL Scientific, Inc. The di-(2-amino-2-methyl-1,3-propanediol) salt of MUP (di-Am form of MUP) generally has a lower level of contaminating MU, so minimum background can be achieved by aging about 2 days under the same conditions; the di-sodium salt of MUP generally requires an intermediate time to achieve minimum background. This background reduction capability is highly useful in manufacturing, since lot-to-lot reproducibility can be achieved with the less expensive raw material containing the higher level of hydroxy coumarin contaminant.

The stabilized hydroxy coumarin ester can be used for enzyme assay by mixing it with a substrate buffer suitable for the enzyme assay. The final pH of the resulting enzyme assay milieu should be below 11 and should be appropriate for the enzyme being assayed. The stabilized hydroxy coumarin ester must be converted from its stabilized form back to its enzymatic substrate form before the enzyme can convert it to its corresponding hydroxy coumarin. The rate of this conversion increases with decreasing pH. At a pH of 9.0 the conversion is very fast such that sufficient substrate is generated in the first few seconds. At higher pH values the slower conversion rate may result in a lag phase in the enzyme assay depending upon when the enzyme is added to the assay milieu relative to the addition of the stabilized hydroxy coumarin ester. Common enzyme assay buffers that can be used include tris (hydroxymethyl) aminomethane (TRIS) buffer, phosphate buffer, N-2-hydroxyethylpiperazine-N'-2-ethane-sulphonic acid (HEPES) buffer, 2-amino-2-methyl-1-propanol (AMP) buffer, diethanolamine (DEA) buffer and carbonate buffer. The preferred buffer for use with stabilized 4-methyl umbelliferyl phosphate and alkaline phosphatase is 2.4M diethanolamine at pH 9.0.

The following examples are intended to illustrate more fully the nature of the invention but do not in any way limit the scope of the invention.

EXAMPLE 1

Stabilization of 4-methyl Umbelliferyl Phosphate in Sodium Hydroxide

Solutions of 15 mM 4-methyl umbelliferyl phosphate (MUP) free acid (JBL Scientific Inc., San Luis Obispo, Calif.) in 0.09N, 0.1N, 0.11N, 0.25N and 0.5N sodium hydroxide were prepared and stored at 4° and 37° C. At different times aliquots were withdrawn for stability measurement by an enzyme assay method and an absorbance method as described below. The results are summarized in Tables 1A and 1B. Only 37° C. results are shown. At 4° C., instability was not detectability over the NaOH concentration range studied. The results indicate that as the concentration of sodium hydroxide increases the MUP becomes more stable. When using 0.25 to 0.5N sodium hydroxide, the MUP appears to be completely stable.

A. Enzyme assay method: 150 μL of the MUP solution under test were added to 750 μL of 2.4M diethanolamine (DEA, Du Pont Co., Wilmington, Del.), pH 9.0, which had been preincubated at 37° C. The milieu was mixed (time=0) and incubated at 37° C. At 10 seconds after mixing 20 μL of a 50 ng/mL ($\sim 2.5 \times 10^{-3}$ unit/mL) solution of alkaline phosphatase was added to the milieu, the milieu was mixed, and then incubated at 37° C. At time=5 min. the reaction was stopped by adding 900 μL of 0.5M ethylenediamine tetraacetic acid (EDTA) solution at pH 9.0. The relative fluorescence was measured on a Photon TM Immunoassay analyzer where the excitation wavelength was at 360 nm and emission wavelength was at 450 nm (Hybritech Inc., San Diego, Calif.).

TABLE 1A

Stabilization of MUP in NaOH at 37° C.
Enzyme Assay Method

| NaOH Conc. Day 10 F. Unit | Day 1 F. Unit | Day 3 F. Unit | |
|---|---|---|---|
| 0.09 N | 1230 | 1050 | 810 |
| 0.10 N | 1150 | 1130 | 885 |
| 0.11 N | 1215 | 1105 | 960 |
| 0.25 N | 1216 | 1214 | 1260 |
| 0.5 N | 1310 | 1240 | 1240 |

B. Absorbance method: Thirty μL of the MUP solution under test was added to 2 mL of 1N hydrochloric acid, incubated at room temperature for 5 min. and the absorbance at 312 nm was measured on an HP 8450 Diode Array Spectrophotometer (Hewlett Packard, Palo Alto, Calif.). The acid pH was used to achieve complete conversion to the active substrate form quickly for the sake of convenience. The substrate was stable for about 30 minutes at the acid pH after which measurable self-hydrolysis started. The absorbance at 312 nm measured the level of 4-methyl umbelliferyl phosphate.

TABLE 1B

Stabilization of MUP in NaOH at 37° C.
Absorbance Method

| NaOH Conc. | Day 0 ($A_{312}$) | Day 3 ($A_{312}$) | Day 10 ($A_{312}$) |
|---|---|---|---|
| 0.09 N | 2.29 | 2.00 | 1.53 |
| 0.10 N | 2.29 | 2.07 | 1.70 |
| 0.11 N | 2.24 | 2.04 | 1.81 |
| 0.25 N | 2.25 | 2.21 | 2.23 |
| 0.5 N | 2.34 | 2.32 | 2.33 |

EXAMPLE 2

Background Reduction of MUP in Sodium Hydroxide

Solutions of 15 mM MUP free acid and MUP di-(2-amino-2-methyl-1,3-propanediol) salt (di-Am salt)were prepared in each of 1M TRIS buffer pH 8.0, 2.4M DEA buffer pH 9.0, 0.1N sodium hydroxide and 0.5N sodium hydroxide. The solutions were stored at room temperature. At the indicated time 300 μL of the MUP solution under test was mixed with 1.7 mL of 2.4M DEA pH 9.0 and incubated at room temperature for 4 minutes. The relative fluorescence was then measured on a Sequoia-Turner Model 400 Fluorometer where the excitation wavelength was at 360 nm and emission wavelength was at 415 nm (Sequoia-Turner, Mt. View, Calif.). The results are summarized in Table 3 and indicate that the background fluorescence increases with time when the MUP is stored in the lower pH buffers (TRIS and DEA) while the background fluorescence actually decreases with time when the MUP is stored in 0.1 or 0.5N sodium hydroxide. In fact, degradation of the substrate was too rapid to conduct any stability studies in TRIS and DEA buffers. The variable aging time required for background reduction is seen primarily due to the variable levels of the contaminant in the acid and diammonium forms of the substrate.

TABLE 2

Background Reduction of MUP in Sodium Hydroxide

| Buffer | MUP | Fluorescence Units at | | | | |
|---|---|---|---|---|---|---|
| Time | form | 1 hr. | 18 hr. | 24 hr. | 90 hr. | 192 hr. |
| TRIS pH 8.0 | acid | 132 | ND | 350 | 1350 | ND |
| DEA pH 910 | acid | 140 | ND | 360 | 1180 | ND |
| 0.1 N NaOH | acid | 270 | 60 | 39 | 8 | 8 |
| 0.5 N NaOH | acid | 196 | 41 | 34 | 10 | 7 |
| 0.1 N NaOH | Di-Am | 20 | 16 | 14 | 8 | 9 |
| 0.5 N NaOH | Di-Am | 16 | 7 | 7 | 6 | 6 |

EXAMPLE 3

Stabilization of 4-methyl umbelliferyl β-D-galactopyranoside In Sodium Hydroxide Solution Solutions of 3 mM 4-methyl umbelliferyl β-D-galactopyranoside (MUG) were prepared in 1M TRIS pH 8.0, 0.1N sodium hydroxide and 0.5N sodium hydroxide. The solutions were stored at 37° C. and the stability of the ester in the various solutions was monitored by diluting 50 μL of the solution under test with 2 mL of 1N hydrochloric acid, incubating at room temperature for 3 min. and measuring the absorbance at 316 nm. The results are summarized in Table 3 and indicate that MUG is also stabilized by high pH. Additionally, the low solubility problem of MUG in TRIS is overcome by the use of base.

TABLE 3

Stabilization of MUG in NaOH at 37° C.

| Solution | Day 0 ($A_{312}$) | Day 2 ($A_{312}$) | Day 4 ($A_{312}$) | Day 7 ($A_{312}$) |
|---|---|---|---|---|
| MUG in TRIS pH 8.0* | 0.95 | 0.85 | 0.82 | 0.88 |
| MUG in 0.1 N NaOH# | 1.09 | 1.02 | 1.01 | 1.14 |
| MUG in 0.5 N NaOH# | 1.01 | 1.06 | 1.08 | 1.14 |

*Partly soluble suspension
Clear solution

EXAMPLE 4

Stabilization 4-methyl Umbelliferyl Phosphate in Guanidine Buffer

Aliquots of a solution of 4 mM 4-methyl umbelliferyl phosphate disodium salt (Biosynth International, P.O. Box 541, Skokie, Ill., 60077) prepared in 10 mM guanidine buffer, pH 13.0 were stored at 4 and 37 degrees C. The aliquots of the substrate solution were then taken out on different days and used in a chromium dioxide magnetic particle based immunoassay for Thyroid Stimulating Hormone (TSH). The TSH assay was developed using a sandwich format with two distinct site monoclonal antibodies, the capture antibody being directed against the alpha-beta combining site and the conjugate antibody against the beta subunit. The chromium dioxide-antibody particles and alkaline phosphatase-conjugated antibodies were prepared similarly to the procedure published in Clin. Chem. Vol. 33, 1543–1547, 1987. Ten microliters of the conjugate were added to 50 microliters of TSH samples at zero and 50 micro IU/ml levels (duplicate tubes at each level) and incubated for 10 minutes at 37 degrees C. To the reaction mixture were added 10 microliters of the antibody-coupled particles followed by an additional incubation for 10 min. The reaction mixtures were washed three times, each with 500 microliters of a wash buffer consisting of 80 mM NaCl and 0.1% Tween 20, pH 6.0. The wash procedure was as described in the above mentioned Clin. Chem. reference. The working substrate solution was prepared by diluting the 4-methyl umbelliferyl phosphate stock solution in guanidine buffer 1:40 fold into 1M diethanolamine (DEA) substrate buffer, pH 8.9. One hundred microliters of the substrate solution were added to each of the washed particles, the mixtures were incubated for 5 minutes, then quenched by the addition of 1 ml of 50 mM EDTA solution, pH 10.1. The quenched solutions were transferred into cuvettes after magnetic separation of the particles and fluorescence of the supernatants was measured on a Perkin Elmer Model LS 2B filter fluorometer with the excitation wavelength at 375 nm and the emission wavelength at 450 nm. Assay results with the substrates stored at 4 and 37 degrees are summarized in Table 4.

TABLE 4

TSH Assay Using 4-Methyl Umbelliferyl Phosphate Stabilized in Guanidine Buffer

| TSH Level μIU/ml | Day 0 | Day 4 | Day 7 | Day 11 | Day 14 |
|---|---|---|---|---|---|
| 4 degrees C. | | | | | |
| 0 | 53.1 | 80.9 | 59.9 | 57.1 | 44.8 |
| 50 | 1252 | 1250 | 1263 | 1308 | 1204 |
| 37 degrees C. | | | | | |
| 0 | 53.1 | 81.2 | 54.4 | 47.9 | 48.2 |
| 50 | 1252 | 1284 | 1247 | 1285 | 1251 |

The Day "0" assay results using the substrate prepared in 0.1N NaOH were comparable to those in Table 4 with 38.9 for the zero level and 1187 for the 50 level samples.

The data demonstrate that the substrates stored in 10 mM guanidine buffer, pH 13.0 are as stable as those stored in 0.1N NaOH, pH 12.6. Thus, it is concluded that it is likely the level of OH ion, not NaOH that is important in stabilizing the hydroxy coumarin esters. The results also demonstrate the possibility for storing the stabilized substrate solution on an automated instrument for at least 14 days at 37 degrees C. This permits more flexibility for the design of an instrument with fluorescence detection.

EXAMPLE 5

Tabletting Of 4-Methyl Umbelliferyl Phosphate in 0.1N Sodium Hydroxide

Substrate tablets were prepared by the known SI process (U.S. Pat. Nos. 3,721,725, 3,928,566, and 3,932,943) to provide means for long-term stability. The tablet blend prepared from a liquid mixture included 0.461 mg 4-methyl umbelliferyl phosphate, 4 mg NaOH, 42.54 mg trehalose and 3 mg carbowax per tablet such that when hydrated with 1.0 ml $H_2O$ per tablet, it produced 1.3 mM substrate in 0.1N NaOH, pH 12.6. After hydration of each tablet and storage at 4° C., fresh aliquots were taken out on different days and used in the above described TSH assay. The only difference a substrate preparation which involved hydrating the tablet with 500 microliters water and taking 50 microliters of that aliquot into 1.15 ml of 1M DEA, pH 8.9 buffer to give 0.1 mM MUP in the assay. Results are shown in Table 5.

TABLE 5

| TSH, µIU/ml | Day 0 | Day 1 | Day 3 | Day 6 | Day 8 | Day 16 | Day 17 |
|---|---|---|---|---|---|---|---|
| 0 | 39.0 | 33.4 | 39.6 | 35.0 | 55.4 | 39.7 | 35.1 |
| 5 | 240.2 | 254.1 | 268.8 | 232.2 | 256.1 | 282.0 | 268.0 |
| 25 | 895.3 | 904.6 | 1002.3 | 854.2 | 875.0 | 939.5 | 881.2 |

The results indicate the hydrated substrate tablet stability in the TSH assay to be as good as that of the substrate solution before tabletting. That means that the excipients play no part in the stability of the substrate, an important demonstration for tablettability.

Tablets can also be prepared by the process of fluid-bed-spray granulation. In this process the powders are brought to a fluidized state by directing heated air upward through the material in the product container. After the powders containing excipients are sufficiently mixed, a granulating liquid containing the substrate prepared in base is sprayed onto the particles; fluidization and spraying are continued until an agglomerate of desired size is formed. This process results in particles that are relatively dense, exhibiting good flow and compressibility. However, the tablets prepared by the fluid-bed-spray granulation process may exhibit compromised dissolution times because the particles are dense. Tablet blends prepared by the S-1 process have resulted in tablets with considerably faster dissolution times. The S-1 process involves spraying a solution of the tablet excipients and the substrate in base into a moving bath of Freon® fluorocarbon, collecting the frozen particles and freeze-drying them. This results in a blend with a lower bulk density and more porous particles which accounts for faster dissolution (all other things being equal). The S-1 process is more time-consuming and costly than the fluid-bed-spray granulation process. The substrate may be aged before or after hydration of the tablets.

We claim:

1. A method of stabilizing a hydroxy coumarin ester against hydrolysis to a hydroxy coumarin which comprises dissolving the ester in water containing a strong base in sufficient concentration to bring the hydroxy coumarin and base solution to a $pH \geq 11$ to stabilize the ester against hydrolysis.

2. Method of claim 1 wherein the hydroxy coumarin ester is initially contaminated with hydroxy coumarin and the solution is aged long enough to reduce the level of hydroxy coumarin in the solution.

3. Method of claim 2 wherein the solution is aged long enough to substantially eliminate the hydroxy coumarin and achieve minimum background fluorescence.

4. Method of claim 3 wherein the ester is a member of the group consisting of 4-methyl umbelliferyl phosphate, acetate, sulfate, oleate, $\beta$-D-galactopyranoside, p-guanidinobenzoate, and salts thereof, and the final pH of the solution is $>11$.

5. Method of claim 4 wherein the ester is 4-methyl umbelliferyl phosphate or a salt thereof and the final pH of the solution is $>12.5$.

6. Method of claim 5 wherein the base is sodium hydroxide at a concentration in the range of 0.1N to 1N.

7. Method of claim 5 wherein the base is guanidine and the solution is buffered to a pH of about 13.

8. Method of any one of claims 1 through 7 further comprising drying the solution to provide a powder mixture of the stabilized ester and the base and tabletting the powder mixture.

9. A solution prepared by the process of any one of claims 1 through 7.

10. A tablet prepared by the process of claim 8.

* * * * *